United States Patent
Sasagawa et al.

(10) Patent No.: US 7,419,471 B2
(45) Date of Patent: Sep. 2, 2008

(54) ARM INSERTION TYPE SPHYGMOMANOMETER

(75) Inventors: Hiroki Sasagawa, Fujinomiya (JP); Katsumi Tsukuda, Fujinomiya (JP); Hitoshi Ozawa, Fujinomiya (JP); Shinichi Takahira, Tokyo (JP)

(73) Assignee: Terumo Kabushiki Kaisha, Shibuya-ku, Tokyo (JP)

( * ) Notice: Subject to any disclaimer, the term of this patent is extended or adjusted under 35 U.S.C. 154(b) by 0 days.

(21) Appl. No.: 10/588,026

(22) PCT Filed: Jan. 28, 2005

(86) PCT No.: PCT/JP2005/001182

§ 371 (c)(1), (2), (4) Date: Nov. 8, 2006

(87) PCT Pub. No.: WO2005/074793

PCT Pub. Date: Aug. 18, 2005

(65) Prior Publication Data

US 2007/0167845 A1    Jul. 19, 2007

(30) Foreign Application Priority Data

Feb. 3, 2004   (JP)   ............... 2004-027107
Apr. 9, 2004   (JP)   ............... 2004-115794

(51) Int. Cl.
*A61B 5/02*   (2006.01)
(52) U.S. Cl. ................... 600/490; 600/485
(58) Field of Classification Search ........... 600/485, 600/490–503
See application file for complete search history.

(56) References Cited

U.S. PATENT DOCUMENTS 5,687,732 A * 11/1997 Inagaki et al. ............ 600/485
(Continued)

FOREIGN PATENT DOCUMENTS

JP     5-056938 A    3/1993
(Continued)

OTHER PUBLICATIONS

Form PCT/IB/373 (International Preliminary Report on Patentability, English translation only).
(Continued)

*Primary Examiner*—Robert L. Nasser, Jr.
*Assistant Examiner*—Karen E Toth
(74) *Attorney, Agent, or Firm*—Buchanan Ingersoll & Rooney PC

(57) ABSTRACT

An arm insertion type sphygmomanometer having enhanced operability and visibility at the time of measurement. A remote control unit can be detached from the sphygmomanometer body portion and operated wirelessly. The arm insertion type sphygmomanometer comprises a sphygmomanometer body portion (10) provided with an arm band (2) through which an upper arm is inserted, and a remote control unit (40) capable of controlling the sphygmomanometer body portion (10) remotely. The remote control unit (40) can be fixed removably to a holding portion (5) of the sphygmomanometer body portion (10) and has an operating portion for operating the sphygmomanometer body portion (10), and a display portion for displaying the result of measurement. In a state where the remote control unit (40) is placed in the holding portion (5), the remote control unit (40) operates the sphygmomanometer body (10) by performing wired or wireless communication therewith. In a state where the remote control unit (40) is not placed in the holding portion (5), the remote control unit (40) operates the sphygmomanometer body (10) by performing wireless communication therewith.

6 Claims, 9 Drawing Sheets

U.S. PATENT DOCUMENTS

| | | | |
|---|---|---|---|
| 6,251,080 B1* | 6/2001 | Henkin et al. | 600/490 |
| 6,344,025 B1 | 2/2002 | Inagaki et al. | |
| 6,432,061 B1* | 8/2002 | Nissila et al. | 600/500 |
| 6,475,153 B1* | 11/2002 | Khair et al. | 600/485 |
| 6,506,162 B1* | 1/2003 | Tseng | 600/485 |
| 2005/0187484 A1* | 8/2005 | Sano et al. | 600/495 |
| 2006/0079792 A1* | 4/2006 | Finburgh et al. | 600/485 |
| 2006/0253041 A1* | 11/2006 | Shin et al. | 600/493 |

FOREIGN PATENT DOCUMENTS

| | | |
|---|---|---|
| JP | 5-137697 A | 6/1993 |
| JP | 10-080401 A | 3/1998 |
| JP | 2000-083912 A | 3/2000 |

OTHER PUBLICATIONS

Form PCT/ISA/237 (Written Opinion of the International Searching Authority, English translation only).
Form PCT/ISA210 (International Search Report) dated Mar. 8, 2005.
Form PCT/ISA/237 (Written Opinion of the International Searching Authority) dated Mar. 8, 2005.

* cited by examiner

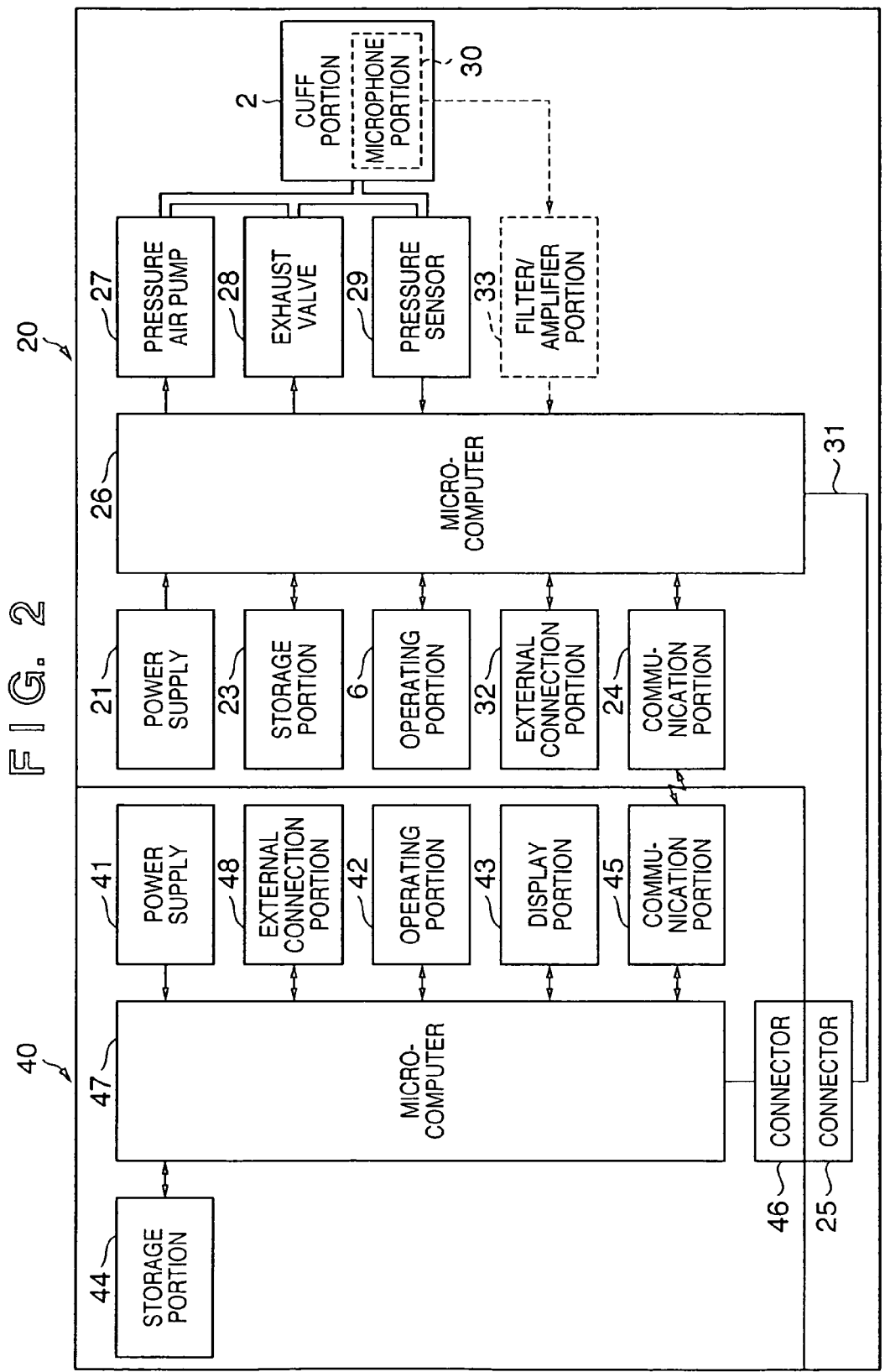

FIG. 3

| D1 | D2 | D3 | D4 | D5 D6 | D7 | D8 | D9 | D10 |
|---|---|---|---|---|---|---|---|---|
| IDENTIFI- CATION NUMBER | MEASURE- MENT DATE | BLOOD PRESSURE VALUE (MAXIMUM VALUE/ MINIMUM VALUE) | PULSE RATE | BODY TEMPERATURE/ BODY WEIGHT | BLOOD GLUCOSE LEVEL | DRUG NAME | MOTION AMOUNT | PULSE PRESSURE (MAXIMUM BLOOD PRESSURE- MINIMUM BLOOD PRESSURE) |
| ......... | ......... | ......... | ......... | ......... | ......... | ......... | ......... | ......... |

ARM INSERTION TYPE SPHYGMOMANOMETER

TECHNICAL FIELD

The present invention relates to an arm insertion type sphygmomanometer which is designed such that an arm band through which the upper arm of a person to be measured is inserted is incorporated in a sphygmomanometer body portion so as to eliminate the necessity of winding the arm band around the upper arm of the person, and can perform sphygmomanometry on either the left or right upper arms.

BACKGROUND ART

Conventionally, an arm insertion type sphygmomanometer installed in a hospital or the like is designed such that one of the upper arms (e.g., one that is not the dominant arm) of a person to be measured is inserted into an opening portion surrounded by an arm band, and a blood pressure is measured by operating an operating portion such as a measurement start switch with the other hand. If, however, the other arm is disabled, it is very difficult to perform such operation.

In some sphygmomanometer of a type designed to wind an arm band, the arm band is separated from a sphygmomanometer body portion (see, for example, patent references 1 and 2):

Patent document 1: Japanese Patent Laid-Open No. 5-56938

Patent document 2: Japanese Patent Laid-Open No. 5-137697

DISCLOSURE OF INVENTION

Problems that the Invention is to Solve

According to patent references 1 and 2 as well, if one arm is disabled, it is difficult to insert an arm into an arm band and wind it around the arm.

The present invention has been made in consideration of the above problem, and has as its object to provide an arm insertion type sphygmomanometer which allows a user to wirelessly operate a sphygmomanometer body portion with a remote control unit upon detaching it therefrom, and can improve operability and visibility at the time of measurement.

It is another object of the present invention to provide an arm insertion type sphygmomanometer which can be carried about as a memory with a display and can help cooperation with a medical site such as a family doctor.

Means of Solving the Problems

In order to solve the above problems and achieve the objects, an arm insertion type sphygmomanometer of the present invention comprises a sphygmomanometer body portion provided with an arm band in which an upper arm is inserted, and a remote control unit which allows remote control of the sphygmomanometer body portion, characterized in that the remote control unit includes an operating portion which is detachably mounted on a holding portion of the sphygmomanometer body portion and operates the sphygmomanometer body portion, and a display portion which displays a measurement result, the remote control unit operates the sphygmomanometer body portion by wired or wireless communication with the sphygmomanometer body portion while the remote control unit is stored in the holding portion, and the remote control unit operates the sphygmomanometer body portion by wireless communication with the sphygmomanometer body portion while the remote control unit is not stored in the holding portion.

Preferably, the remote control unit comprises a storage portion which stores identification information of each person to be measured, sphygmomanometry date information, and blood pressure value for each measurement data or pulse rate value (pulse rate) or trend information thereof, and the communication portion acquires the information and the display portion displays the information.

In addition, preferably, the sphygmomanometer body portion comprises an operating portion which operates the sphygmomanometer body portion, a display portion which displays a measurement result, a communication portion which allows wireless communication with the remote control unit, and a storage portion which stores identification information unique to each person to be measured, sphygmomanometry date information, and blood pressure value for each measurement date or pulse rate value (pulse rate) or trend information thereof, the remote control unit outputs an operation signal to the sphygmomanometer body portion, and the sphygmomanometer body portion generates each information on the basis of an operation signal received from the remote control unit and outputs the information to the remote control unit.

Furthermore, preferably, the display portion is stored in the sphygmomanometer body portion in a position that allows a person to be measured to visually recognize the display portion during measurement.

Moreover, preferably, the arm insertion type sphygmomanometer further comprises a holding unit which holds the sphygmomanometer body portion, the holding unit having a function of adjusting the posture of the sphygmomanometer body portion or a function of allowing measurement at a proper region.

Effect of the Invention

As described above, according to the present invention, since the remote control unit can be detached from the sphygmomanometer body portion and used for wireless operation, even if one arm of a user is disabled, operability and visibility at the time of sphygmomanometry can be improved by operating the remote control unit with the other arm (to be measured) or placing the remote control unit at a position where the user can operate it.

BRIEF DESCRIPTION OF DRAWINGS

The accompanying drawings, which are incorporated in and constitute a part of this specification, illustrate the embodiments of the present invention and, together with the description, serve to explain the principles of the invention.

FIG. 1A is a perspective view showing an arm insertion type sphygmomanometer according to the first embodiment of the present invention in a state wherein a remote control unit is attached;

FIG. 1B is a perspective view showing the arm insertion type sphygmomanometer according to the first embodiment of the present invention in a state wherein the remote control unit is detached;

[FIG. 2] FIG. 2 is a functional block diagram of the arm insertion type sphygmomanometer according to the first embodiment of the present invention;

[FIG. 3] FIG. 3 is a view exemplifying information stored in the memory portion of a remote control unit;

FIG. 4 is a perspective view showing an arm insertion type sphygmomanometer according to the second embodiment of the present invention in a state wherein a remote control unit is attached;

FIG. 5 is a functional block diagram of the arm insertion type sphygmomanometer according to the second embodiment of the present invention;

FIG. 6A is a perspective view of an arm insertion type sphygmomanometer held on a holding unit according to the fourth embodiment of the present invention, showing a state wherein the arm insertion type sphygmomanometer is not mounted on the holding unit;

FIG. 6B is a perspective view of the arm insertion type sphygmomanometer held on a holding unit according to the fourth embodiment of the present invention, showing a state wherein the arm insertion type sphygmomanometer is mounted on the holding unit;

FIG. 6C is a perspective view of the arm insertion type sphygmomanometer held on the holding unit according to the fourth embodiment of the present invention, showing a member which couples the arm insertion type sphygmomanometer to the holding unit;

FIG. 7 is a functional block diagram of an arm insertion type sphygmomanometer according to the third embodiment of the present invention; and

FIG. 8 is a view showing an example of a display portion according to the embodiment of the present invention.

DESCRIPTION OF THE REFERENCE NUMERALS

Figure 1A:
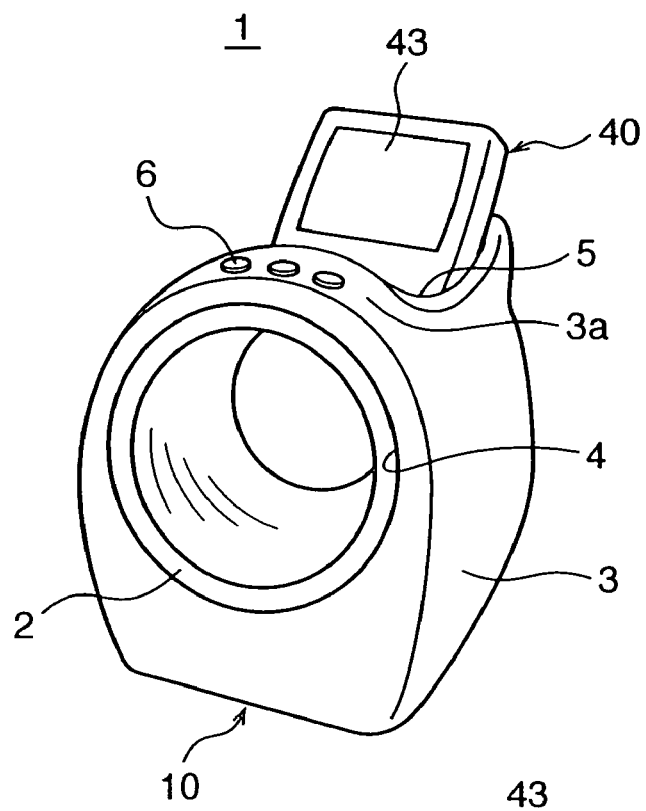
[FIG. 1A]

1: arm insertion type sphygmomanometer
2: cuff portion
3, 13: housing
4: opening portion
5, 15: holding portion
6, 42: operating portion
14, 43: display portion
20, 50: control unit
21, 41: power supply
23, 44: storage portion
24, 45: communication portion
25, 46: connector
26, 47: microcomputer
27: pressure air pump
28: exhaust valve
29: pressure sensor
30: microphone portion
31: communication line
32, 48: external connection portion
33: filter/amplifier portion
35: computation clock circuit
36: timepiece clock circuit
37: radio reception circuit
40: remote control unit
60: holding unit
61: arm rest
62: holding portion

BEST MODE FOR CARRYING OUT THE INVENTION

The embodiments of the present invention will be described in detail with reference to the accompanying drawings.

Each embodiment described below is an example of a means for implementing the present invention. The present invention can be applied to modifications and the like of the embodiments described below within the spirit and scope of the invention.

First Embodiment

Figure 1B:
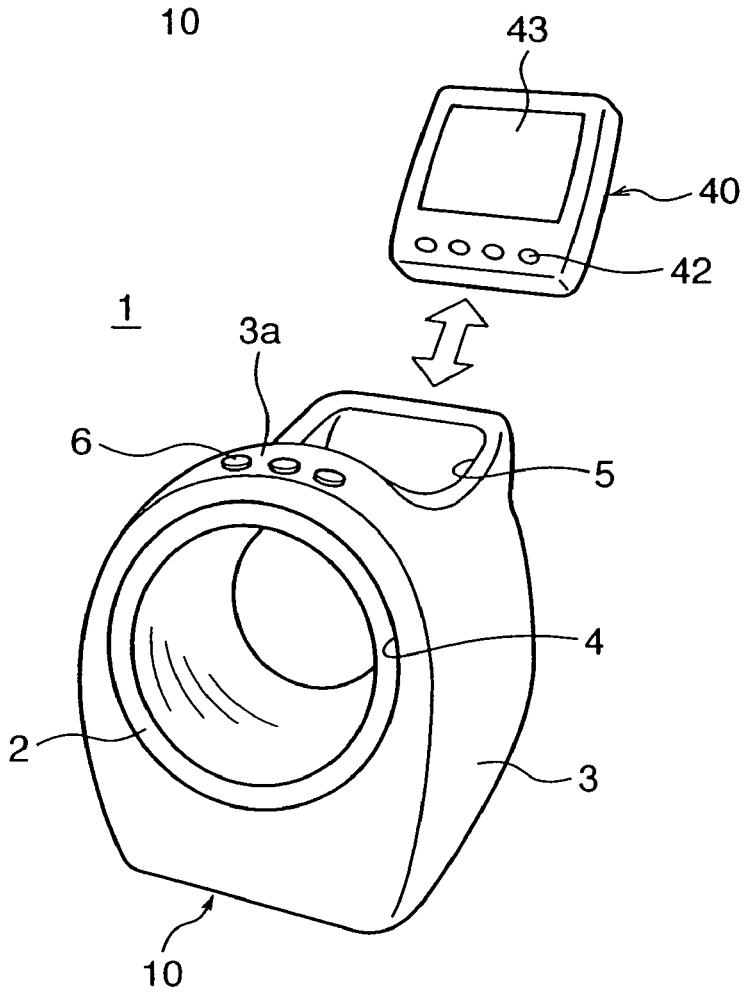
[FIG. 1B]

FIGS. 1A and 1B are perspective views of an arm insertion type sphygmomanometer according to the first embodiment of the present invention. FIG. 1A shows a state wherein a remote control unit is attached. FIG. 1B shows a state wherein the remote control unit is detached. FIG. 2 is a functional block diagram of the arm insertion type sphygmomanometer according to the first embodiment of the present invention.

As shown in FIGS. 1A and 1B, an arm insertion type sphygmomanometer 1 of this embodiment is a sphygmomanometer which has a structure in which a cuff portion 2 as an arm band which presses the upper arm at the time of sphygmomanometry is incorporated in a housing 3 of a sphygmomanometer body portion 10. This sphygmomanometer eliminates the necessity of winding the cuff portion 2 around the upper arm of a person to be measured, and can perform sphygmomanometry on either the left or right upper arm.

The sphygmomanometer body portion 10 is provided with a remote control unit 40 which can remotely control the sphygmomanometer body portion 10. The remote control unit 40 is detachably mounted in a holding portion 5, and includes an operating portion 42 for operating the sphygmomanometer body portion 10 and a display portion 43 which displays a measurement result and the like. The remote control unit 40 has a portable size that allows one-hand operation and can be stored in a pocket of the clothing a person to be measured is wearing. The display portion 43 is designed to display a maximum (systolic) blood pressure value/minimum (diastolic) blood pressure value, pulse rate value (pulse rate), the time, pressurizing operation, depressurizing (evacuating) operation, sphygmomanometric operation, and the like on an LCD or the like. In addition, the remote control unit 40 can store/display the trends of the blood pressure values (maximum (systolic) maximum blood pressure values/minimum (diastolic) blood pressure values) of a plurality of persons to be measured (users), measurement times thereof, and the like by using selection switches, and can also be used for the personal use of one person to be measured (user).

The housing 3 of the sphygmomanometer body portion 10 is provided with an opening portion 4 in which an arm of a person to be measured is to be inserted. The cuff portion 2 comprising a flexible cloth or rubber bag is provided on the inner surface of the opening portion 4. The socket-like holding portion 5 in which the remote control unit 40 is detachably stored and an operating portion 6 comprising an ON/OFF switch and the like are provided on an upper surface portion 3a of the housing 3.

The operating portions 6 and 42 include, for example, a call/cancel switch for stored data, a display switch for a trend graph and the like, and a scroll switch as well as the ON/OFF switch of a power supply and sphygmomanometry start/stop switch.

As shown in FIG. 2, a control unit 20 is mounted in the housing 3 of the sphygmomanometer body portion 10. The control unit 20 comprises, as electrical constituent elements, an AC or DC (battery) power supply 21 which supplies power to the unit, the operating portion 6 which performs operations associated with an ON/OFF switch for starting/stopping the control unit 20 and various kinds of functions, a storage portion 23 comprising a nonvolatile memory or the like which stores sphygmomanometric values obtained by a plurality of number of times of measurement, measurement time data thereof, and the like, a communication portion 24 which allows wireless communication with the remote control unit 40 by using infrared light or radio waves (e.g., Bluetooth), and a connector (or contact) 25 which can be electrically connected to the remote control unit 40 through a communication line. Each of these elements is connected to a microcomputer 26.

The control unit 20 also comprises, as mechanical constituent elements, an air pressurized pump 27 which sends pressurized air to the cuff portion 2 at the start of sphygmomanometry, an exhaust valve 28 which reduces the pressure of the cuff portion 2 at a constant rate and adjusts the pressure of pressurized air by constant or quick evacuation, a pressure sensor 29 which detects the vibration of a blood vessel from fluctuations in the pressure of the cuff, and a microphone portion 30 which detects a blood flow sound. Note that the microphone portion 30 is incorporated in the cuff portion 2. A filter/amplifier portion 33 filters the noise components of the detection signal obtained by the microphone portion 30 and amplifies the signal component after filtering. The amplified signal component is input to the microcomputer 26. The oscillometric method or the Korotkoff sound method can be applied to sphygmomanometry. When sphygmomanometry is to be performed in accordance with the former method, the microphone portion 30 is not required.

The remote control unit 40 comprises, as electrical constituent elements, a DC (battery) power supply 41 which supplies power to the unit 40, the operating portion 42 for performing operations associated with an ON/OFF switch for starting/stopping the control unit 20 and various kinds of functions, the display portion 43 such as a liquid crystal display device which displays a maximum (systolic)/minimum (diastolic) sphygmomanometric value, a pulse rate, a time, and the like, a storage portion 44 comprising a nonvolatile memory which stores sphygmomanometric values corresponding to a plurality of number of times of measurement, measurement time data thereof, and the like, a communication portion 45 which allows wireless communication with the control unit 20 by using infrared light or radio waves (e.g., Bluetooth), and a connector (or contact) 46 which can be electrically connected to the control unit 20 through a communication line 31. Each of these elements is connected to a microcomputer 47.

Each of the microcomputers 26 and 47 of the control unit 20 and remote control unit 40 described above is equipped with a CPU, ROM, RAM, input/output interface circuit, and the like.

As shown in FIG. 1A, while the remote control unit 40 is stored in the holding portion 5 of the sphygmomanometer body portion 10, the two units 20 and 40 are electrically connected to each other through the connectors 25 and 46. The microcomputer 26 of the control unit 20 therefore performs input processing for operation signals from the operating portions 6 and 42 of the control unit 20 and remote control unit 40 through the communication line 31 in accordance with the sequence of a sphygmomanometry program stored in the ROM. In addition, the microcomputer 26 inputs detection signals from the sensors 29 and 30, and outputs driving signals to the air pressurized pump 27 and the exhaust valve 28. Furthermore, the microcomputer 26 determines the measurement values of a blood pressure, pulsation, and the like from detection signals from the pressure sensor 29 and the microphone portion 30, and stores the values in the storage portion 23 of the control unit 20. The microcomputer 26 also outputs these values to the storage portion 44 of the remote control unit 40 through the communication line 31, and outputs a display signal to the display portion 43.

In the stored state shown in FIG. 1A, the control unit 20 charges the power supply 41 of the remote control unit 40 by supplying power thereto through the communication line 31. Note that if the power supply is not a rechargeable battery, there is no need to charge the power supply.

As shown in FIG. 1B, while the remote control unit 40 is not stored in the holding portion 5 of the sphygmomanometer body portion 10, since the wired connection between the two units 20 and 40 through the connectors 25 and 46 is disconnected, the microcomputer 26 of the control unit 20 wirelessly performs input processing for an operation signal from the operating portion 6 of the control unit itself or an operation signal from the operating portion 42 of the remote control unit 40 through the communication portion 45 in accordance with the sequence of the above sphygmomanometry program. The microcomputer 26 also inputs detection signals from the sensors 29 and 30, and outputs driving signals to the air pressurized pump 27 and the exhaust valve 28. In addition, the microcomputer 26 determines the measurement values of a blood pressure, pulsation, and the like from detection signals from the pressure sensor 29 and the microphone portion 30, and stores the values in the storage portion 23. The microcomputer 26 also outputs these values to the remote control unit 40 through the communication portion 24, and outputs a display signal to the display portion 43.

The microcomputer 47 of the remote control unit 40 transmits an operation signal from the operating portion 42 to the control unit 20 through the communication line 31 (at the time of attachment of the remote controller) or through the communication portion 45 (at the time of detachment of the remote controller), and sequentially stores measurement values received from the control unit 20 into the storage portion 44. The microcomputer 47 also performs display control of the display portion 43 on the basis of a display signal.

The control unit 20 acquires and generates various kinds of information such as identification information D1 such as the identification number of each person to be measured, measurement date information D2, a blood pressure value (maximum value/minimum value) D3, a pulse rate D4, a body temperature D5, a body weight D6, a blood glucose level D7, a drug name D8 such as the name of an antihypertensive agent or specified health food, a motion amount (number of steps) D9, and a pulse pressure (=maximum (systolic) blood pressure−minimum (diastolic) blood pressure) D10 as exemplified in FIG. 3 on the basis of operation signals received from the control unit 20, and outputs the pieces of information to the remote control unit 40.

The control unit 20 comprises an external connection portion 32 which can connect to external devices such as a printer for printing out all or an arbitrary combination of the pieces of information D1 to D10 exemplified in FIG. 3 on a blood pressure notebook or the like, a personal computer (PC), and a USB (Universal Serial Bus) memory stick and a measurement device such as a thermometer, weighing machine, blood glucose level measuring device, and pedometer. The control unit 20 can input data from these devices, store them in the storage portion 23, output them to the printer, and download them in the PC.

The remote control unit 40 is also provided with an external connection portion 48 which can connect to external devices such as a personal computer (PC) and a printer and a measurement device such as a thermometer, weighing machine, blood glucose level measuring device, and pedometer. The remote control unit 40 can input data from these devices in the storage portion 44 and store them in the storage portion 44. The remote control unit 40 can also output the data and download them to the PC. Therefore, for example, a doctor can easily print out the measurement value of a blood pressure or the like from the remote control unit 40 which the person to be measured has, and download it to the PC.

In the storage portion 44 of the remote control unit 40, as information acquired from the control unit 20 and other measuring devices, an arbitrary combination of the following pieces of information are stored as trend information, as exemplified by FIG. 3: the identification information D1 such as the identification number of each person to be measured, the measurement date information D2, the blood pressure value (maximum value/minimum value) D3, the pulse rate D4, the body temperature D5, the body weight D6, the blood glucose level D7, the drug name D8 such as the name of an antihypertensive agent or specified health food which each person has taken, the motion amount (number of steps) D9, and the pulse pressure (=maximum (systolic) blood pressure– minimum (diastolic) blood pressure) D10. Pieces of trend information for the respective times of day (or morning, daytime, and evening) stored for a predetermined period of time (e.g., one year) are displayed in the form of a graph or the like on the display portion 43 of the remote control unit 40 by using colors, marks, symbols, or the like with high visibility.

Figure 8:
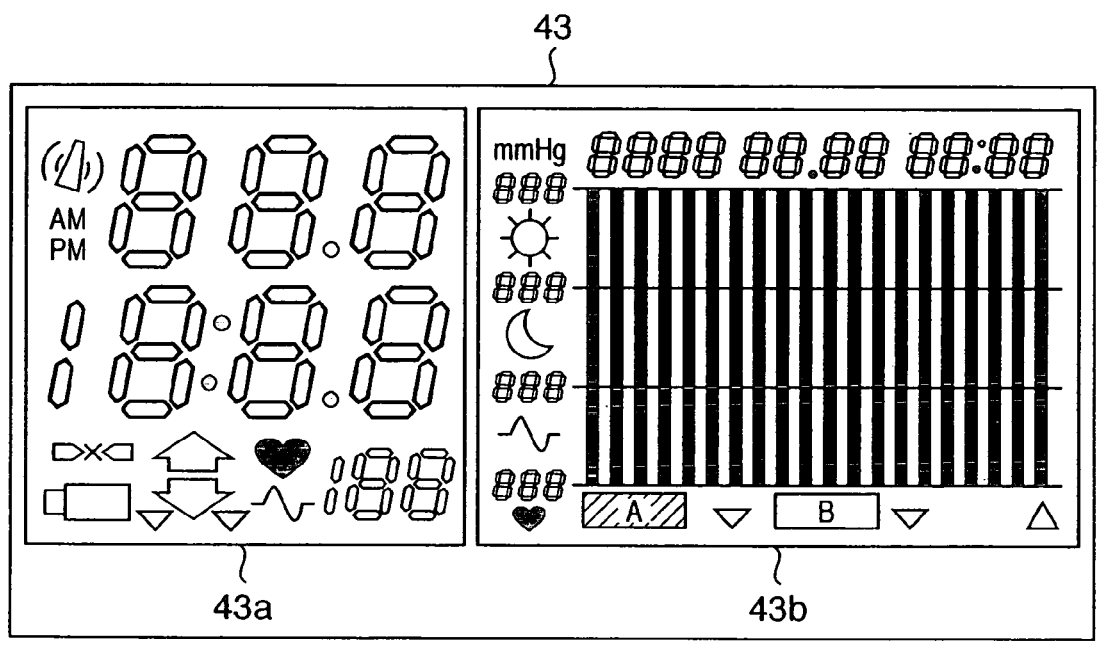
[FIG. 8]

FIG. 8 shows an example of the display portion 43. Reference numeral 43a denotes a display portion which digitally displays a blood pressure value and the like, and displays a low battery alarm and an indication indicating a cuff pressure state; and 43b, a display portion which performs display of the trends of a maximum (systolic) blood pressure, minimum (diastolic) blood pressure, pulse pressure, and the like, and displays notes and the like.

According the above arrangement, if each person has the remote control unit 40, the sphygmomanometer body portion 10 installed in a different place like a place in a hospital can be commonly operated by each remote control unit 40 owned by each person to be measured.

In addition, since the remote control unit 40 can be detached from the sphygmomanometer body portion 10 and the sphygmomanometer body portion 10 can be operated wirelessly, even if one arm is disabled, operability and visibility at the time of sphygmomanometry can be improved by operating the remote control unit 40 with the other arm (the arm to be measured) or placing the remote control unit 40 at a position where the person can operate it.

In addition, since the sphygmomanometer body portion 10 is provided with the operating portion 6 such as an ON/OFF switch like the remote control unit 40, this sphygmomanometer can also be used for sphygmomanometry in a case wherein a person to be measured does not have the remote control unit 40 or wants to know only a current blood pressure. Note that in this case, it suffices to notify the person to be measured of the sphygmomanometry result with a sound by adding a speaker or the like.

Second Embodiment

Figure 4:
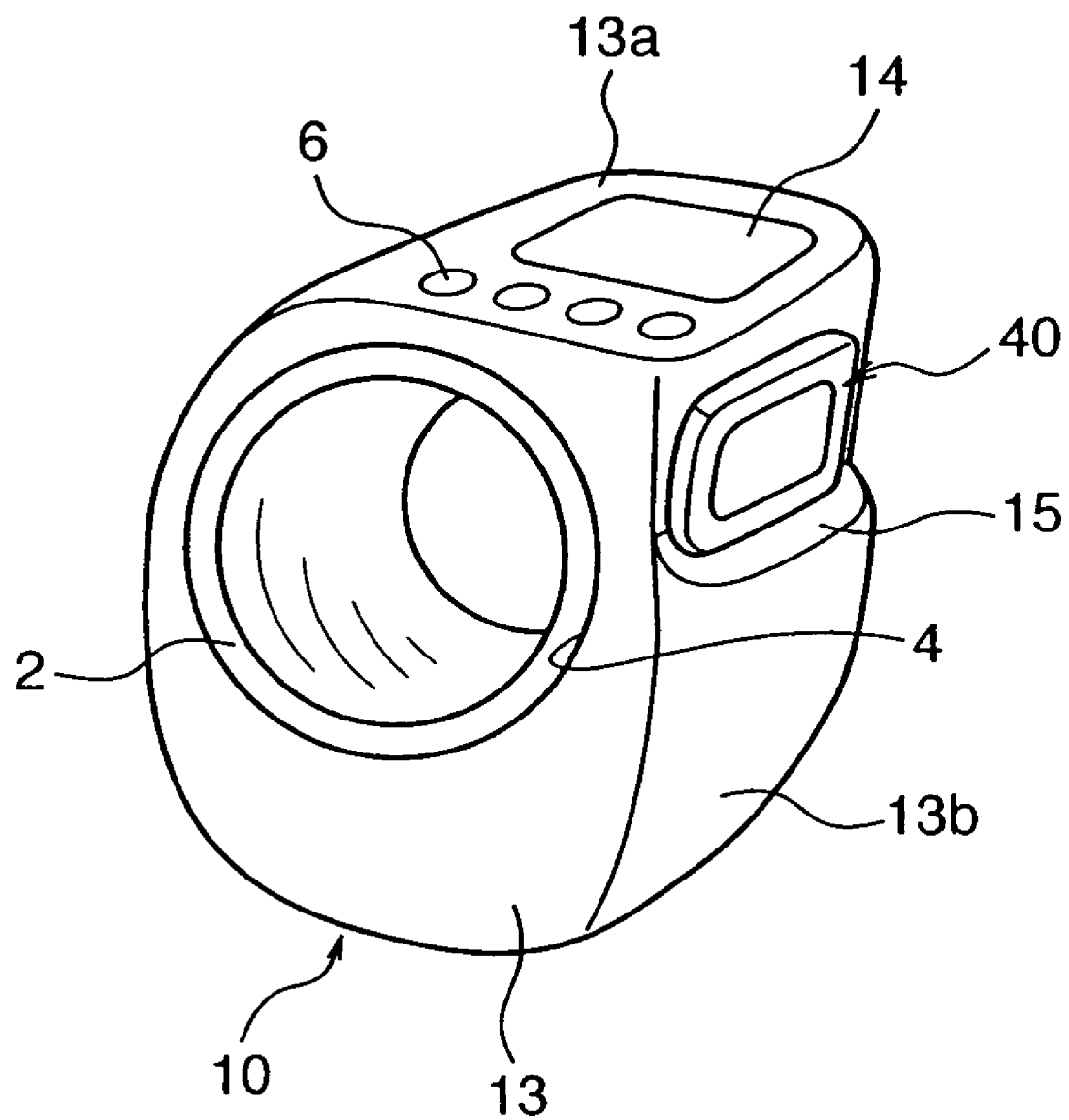
[FIG. 4]

In the case shown in FIGS. 1A and 1B, the display portion 43 is stored in the holding portion 5 in a position to face a person to be measured so as to allow the person to visually recognize the display portion 43 of the remote control unit 40. In the second embodiment shown in FIGS. 4 and 5, a holding portion 15 is provided in a side surface portion 13b of a housing 13, and an operating portion 6 such as an ON/OFF switch and a display portion 14 such as a liquid crystal display device which displays a measured blood pressure value and the like are provided on an upper surface portion 13a of the housing 13.

With regard to other arrangements, the same reference numerals as those in FIGS. 1A to 2 denote elements having the same functions, and a description thereof will be omitted.

In the above arrangement, since the display portion 14 is provided for a sphygmomanometer body portion 10 like a remote control unit 40, this sphygmomanometer can be used for sphygmomanometry in a case wherein a person to be measured does not have the remote control unit 40 or wants to know only a current blood pressure.

In addition, a person to be measured can choose between operating the remote control unit 40 and operating the sphygmomanometer body portion 10, convenience for the person can be improved.

Third Embodiment

Figure 7:
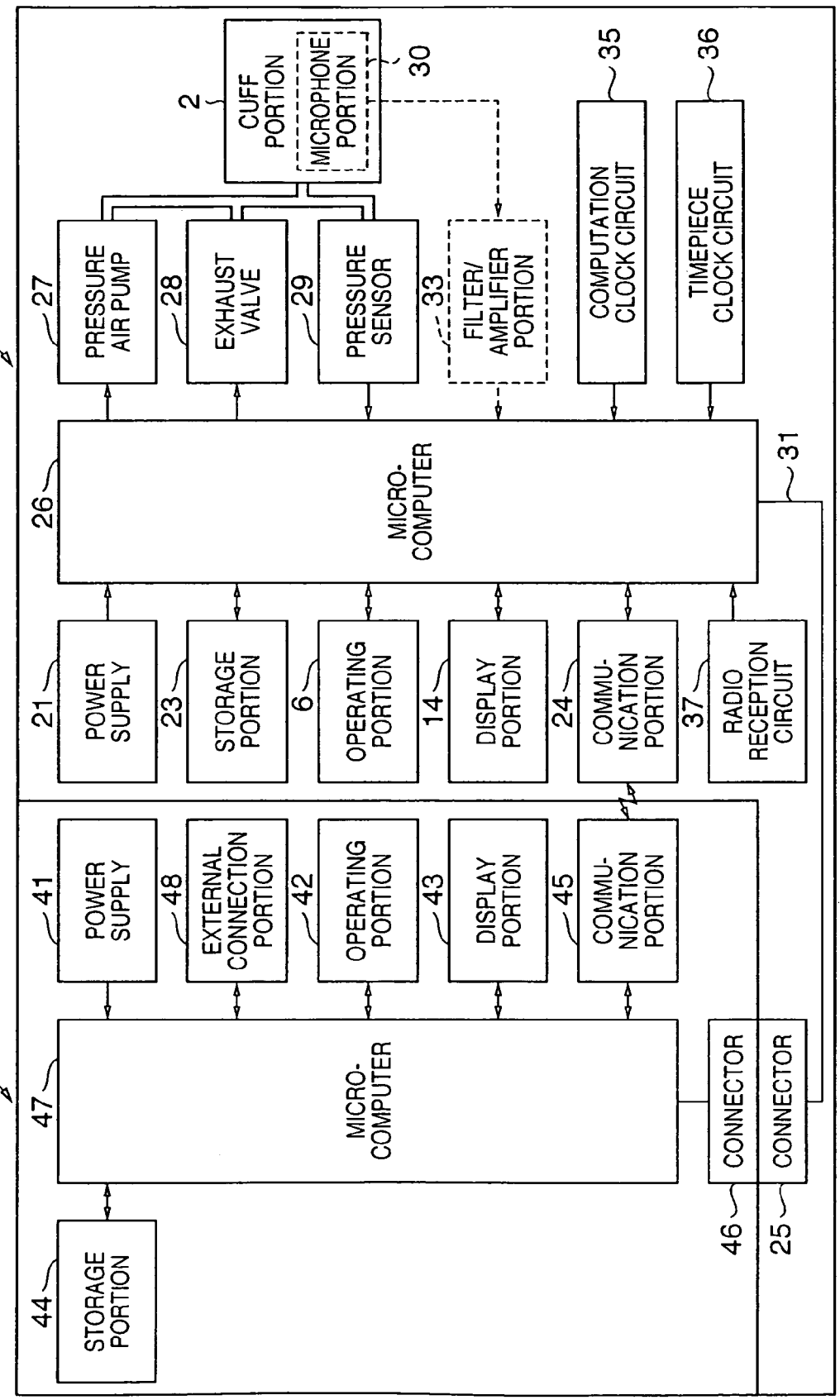
[FIG. 7]

The third embodiment shown in FIG. 7 is obtained by adding a timepiece function to the control unit 20 shown in FIG. 2.

More specifically, the control unit is provided with a computation clock circuit 35, a clock circuit 36 having a timepiece function, an antenna which receives a standard wave, and a radio reception circuit 37 having a function of amplifying, modulating, or the like and is configured to correct the time and always display the correct time on a display portion 43. Note that the timepiece may be controlled to be normally lighted or lighted only when used. In addition, the above timepiece function can also be applied to a control unit 50 in FIG. 5. In this case, the correct time is displayed on a display portion 14 and/or the display portion 43.

Figure 5:
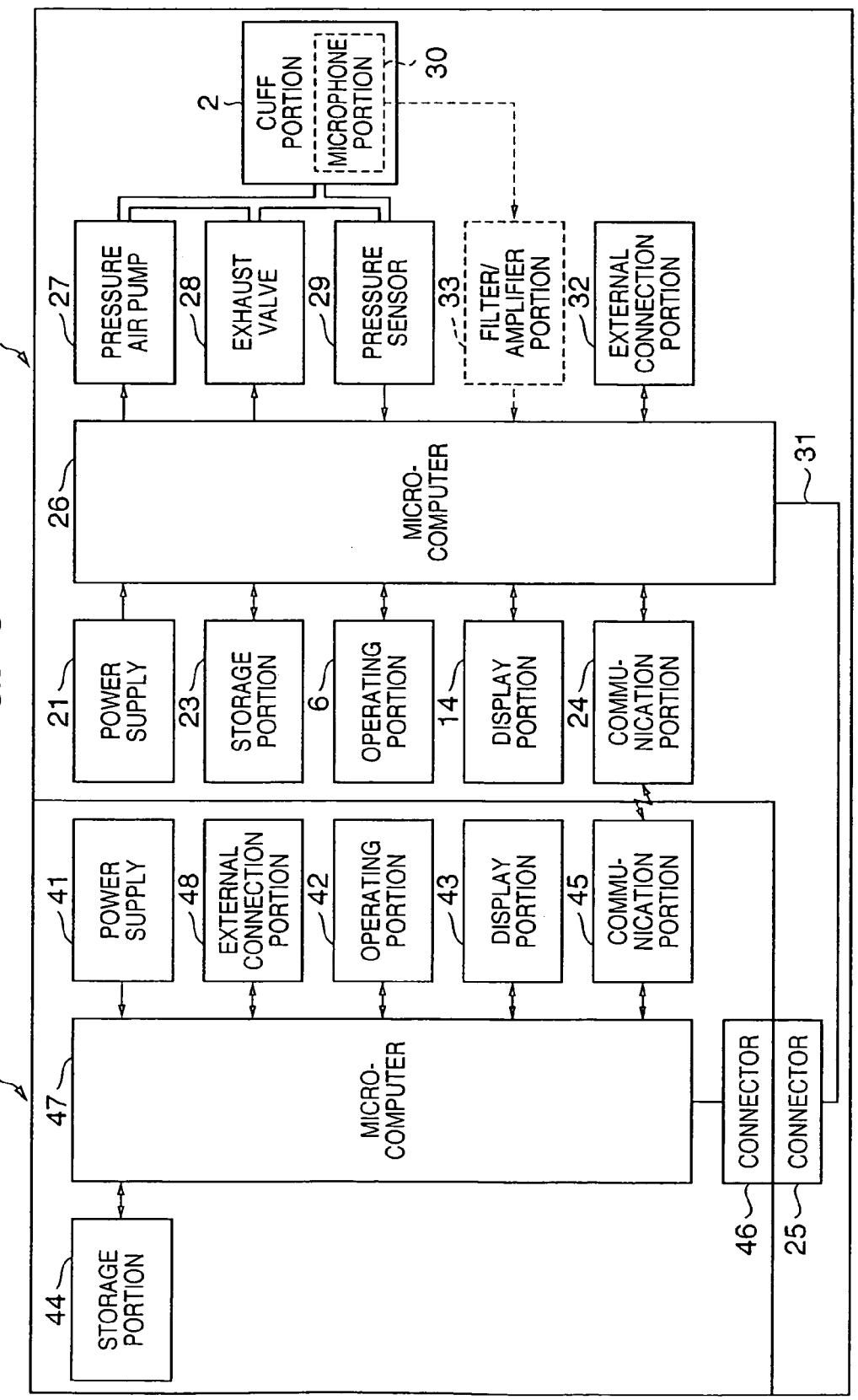
[FIG. 5]

With regard to other arrangements, the same reference numerals as those in FIGS. 1A, 1B, and 5 denote elements having the same functions, and a description thereof will be omitted.

According to the above arrangement, the measurement time of a blood pressure value can be accurately displayed, and the measurement data of blood pressure values corresponding to a plurality of number of times of measurement and the like can be stored together with accurate measurement times, thereby improving convenience for the person to be measured.

Fourth Embodiment

Figure 6A:
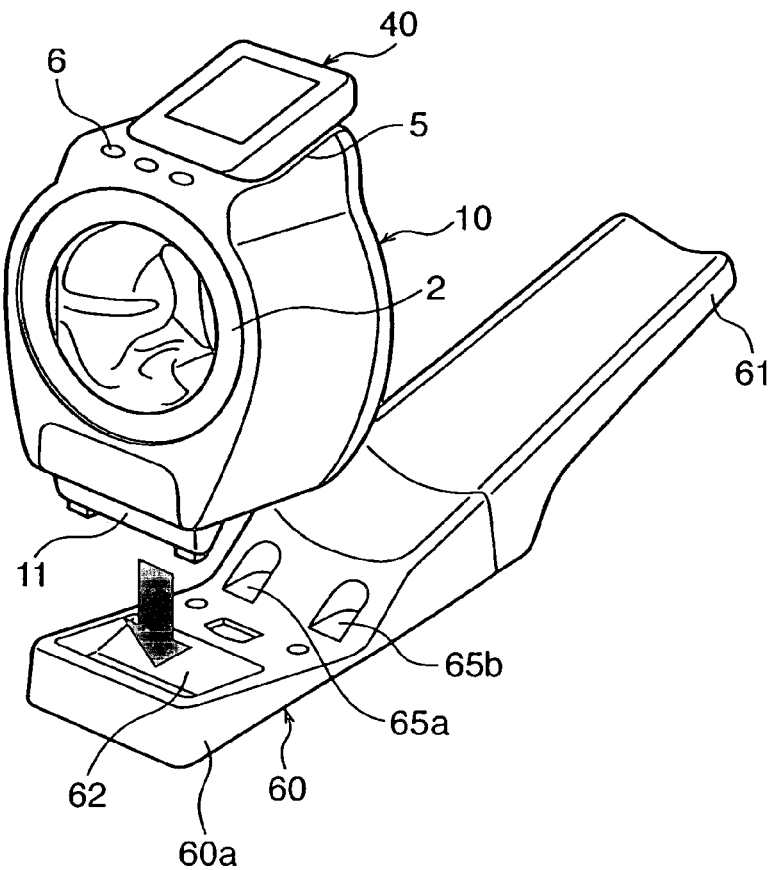
[FIG. 6A]
Figure 6B:
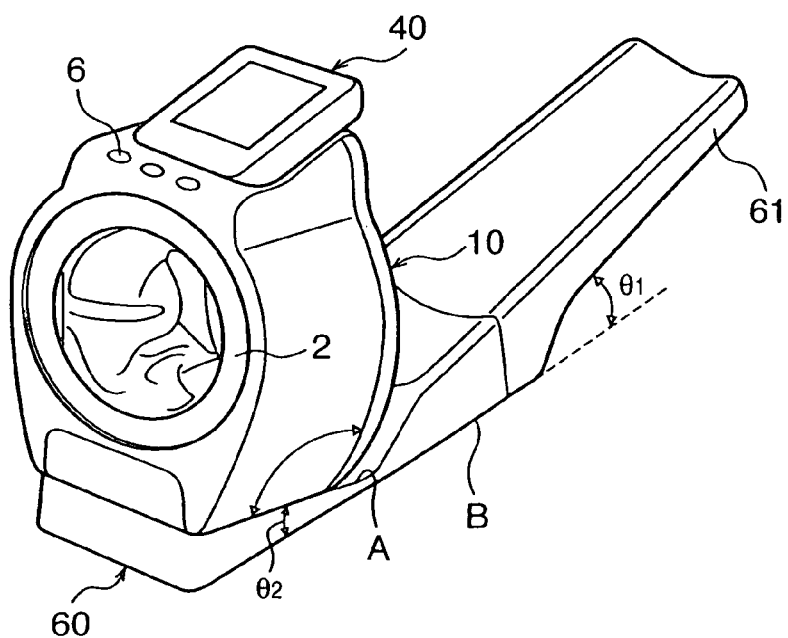
[FIG. 6B]
Figure 6C:
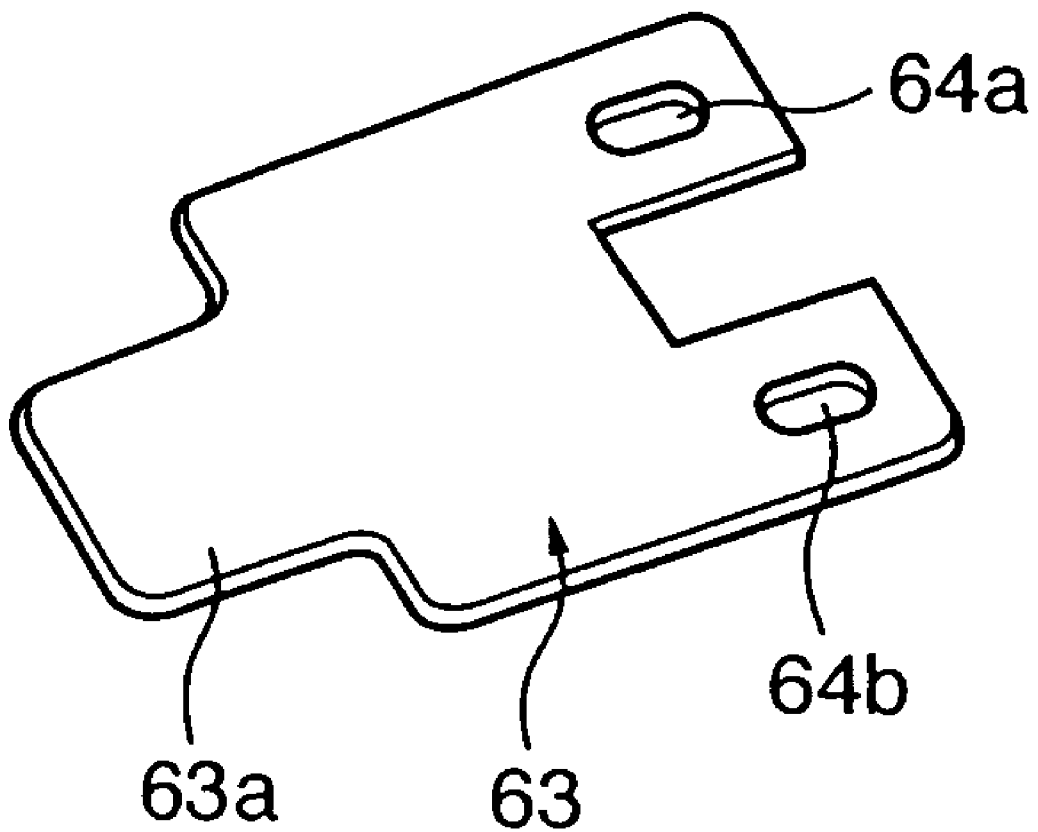
[FIG. 6C]

FIGS. 6A to 6C are perspective views of an arm insertion type sphygmomanometer held on a holding unit according to the fourth embodiment of the present invention. FIG. 6A shows a state wherein the arm insertion type sphygmomanometer is not mounted on the holding unit. FIG. 6B shows a state wherein the arm insertion type sphygmomanometer is mounted on the holding unit. FIG. 6C shows a member which couples the arm insertion type sphygmomanometer to the holding unit.

FIGS. 6A to 6C exemplify an arrangement provided with a holding unit 60 which holds a sphygmomanometer body portion 10 according to each embodiment described above. An arm rest 61 which holds a forearm of a person to be measured is detachably attached to the holding unit 60 and extends therefrom at a predetermined angle θ1 (e.g., 15°) with respect to a bottom surface B. In addition, a concave holding portion 62 having a function of swingably holding the sphygmomanometer body portion 10 on the holding unit 60 and adjusting the posture (the angles and heights in the longitudinal and transverse directions) of the sphygmomanometer body portion 10. The sphygmomanometer body portion 10 is provided with a convex engaging portion 11 which swingably engages with the holding portion 62. When the sphygmomanometer body portion 10 is coupled to the holding unit 60 with a flexible plate-like plastic member 63 or the like so as to make the sphygmomanometer body portion 10 swingable (pivotal) with respect to the holding portion 60, they do not separate from each other, thereby improving portability.

Note that as a coupling method for the sphygmomanometer body portion 10, there is provided a method of providing engaging holes 64a and 64b for the plate-like plastic member 63, providing recess portions 65a and 65b for the holding unit 60, and coupling the sphygmomanometer body portion 10 to the holding unit 60 with screws and the like. In addition, the plate-like plastic member 63 is provided with an extended portion 63a for coupling to the bottom surface of the sphygmomanometer body portion 10. With this arrangement, the sphygmomanometer body portion 10 pivots about a point A in FIG. 6B and tilts to a proper position in accordance with the posture of a person to be measured.

Referring to FIG. 6B, an inclined portion 60a is inclined backward by a predetermined angle θ2 (e.g., 15°) to make the sphygmomanometer body portion 10 tilt backward by θ2. That is, the sphygmomanometer body portion 10 is inclined by a predetermined angle (e.g., 15°) to eliminate the necessity for the user to take a difficult posture.

With regard to other arrangements, the same reference numerals as those in FIGS. 1A and 1B denote elements having the same functions, and a description thereof will be omitted.

The present invention is not limited to the above embodiments and various changes and modifications can be made within the spirit and scope of the present invention. Therefore, to apprise the public of the scope of the present invention the following claims are made.

CLAIM OF PRIORITY

This application claims priority from Japanese Patent Application No. 2004-27107 filed on Feb. 3, 2004 and Japanese Patent Application No. 2004-115794 filed on Apr. 9, 2004, the entire contents of which is hereby incorporated by reference herein.

The invention claimed is:

1. An arm insertion type sphygmomanometer comprising:
a sphygmomanometer body portion provided with an arm band in which an upper arm is to be inserted; and
a remote control unit which allows remote control of said sphygmomanometer body portion, wherein
said remote control unit includes an operating portion which is detachably mounted on a holding portion of said sphygmomanometer body portion and operates said sphygmomanometer body portion, and a display portion which displays a measurement result,
said remote control unit operates said sphygmomanometer body portion by wired or wireless communication with said sphygmomanometer body portion while said remote control unit is stored in the holding portion,
said remote control unit operates said sphygmomanometer body portion by wireless communication with said sphygmomanometer body portion while said remote control unit is not stored in the holding portion,
wherein
said remote control unit comprises a storage portion which stores identification information of each person to be measured, sphygmomanometry date information, and blood pressure value trend information for said each measurement data, and
a communication portion acquires the information and the display portion displays the information.

2. The arm insertion type sphygmomanometer according to claim 1:
wherein
said operating portion is a first operating portions, said display portion is a first display portion, said communication portion is a first communication portion and said storage portion is a first storage portion,
wherein
said sphygmomanometer body portion comprises a second operating portion which operates said sphygmomanometer body portion, a second display portion which displays a measurement result, a second communication portion which allows wireless communication with said remote control unit, and a second storage portion which stores identification information unique to each person to be measured, sphygmomanometry date information, and blood pressure value trend information for said each measurement date,
said remote control unit outputs an operation signal to said sphygmomanometer body portion, and
said sphygmomanometer body portion generates said each information on the basis of an operation signal received from said remote control unit and outputs the information to said remote control unit.

3. The arm insertion type sphygmomanometer according to claim 1:
wherein the display portion is stored in said sphygmomanometer body portion in a position that allows a person to be measured to visually recognize said display portion during measurement.

4. An arm insertion type sphygmomanometer comprising:
a sphygmomanometer body portion provided with an arm band in which an upper arm is to be inserted;
a remote control unit which allows remote control of said sphygmomanometer body portion; and
a holding unit which holds said sphygmomanometer body portion, said holding unit having a function of adjusting the posture of said sphygmomanometer body portion or a function of allowing measurement at a proper region, wherein
said remote control unit includes an operating portion which is detachably mounted on a holding portion of said sphygmomanometer body portion and operates said sphygmomanometer body portion, and a display portion which displays a measurement result,
said remote control unit operates said sphygmomanometer body portion by wired or wireless communication with said sphygmomanometer body portion while said remote control unit is stored in the holding portion,
said remote control unit operates said sphygmomanometer body portion by wireless communication with said sphygmomanometer body portion while said remote control unit is not stored in the holding portion.

5. The arm insertion type sphygmomanometer according to claim 4, wherein said operating portion is a first operating portion and said display portion is a first display portion, and wherein the sphygmomanometer body portion comprises a second operating portion which operates said sphygmomanometer body portion, a second display portion which displays a measurement result, a communication portion which allows wireless communication with said remote control unit, and a storage portion which stores identification information unique to each person to be measured, sphygmomanometry date information, and blood pressure value trend information for said each measurement date,
said remote control unit outputs an operation signal to said sphygmomanometer body portion, and
said sphygmomanometer body portion generates said each information on the basis of an operation signal received from said remote control unit and outputs the information to said remote control unit.

6. The arm insertion type sphygmomanometer, according to claim 4, wherein the display portion is stored in said sphygmomanometer body portion in a position that allows a person to be measured to visually recognize said display portion during measurement.

* * * * *